(12) United States Patent
Drunecky et al.

(10) Patent No.: US 9,474,791 B2
(45) Date of Patent: Oct. 25, 2016

(54) STERILE AUTOLOGOUS, ALLOGENIC OR XENOGENIC IMPLANT AND THE METHOD OF ITS PRODUCTION

(75) Inventors: Tomas Drunecky, Kladno (CZ); Eva Matouskova, Prague (CZ); Petr Stehlicek, Kladno (CZ); Vladimir Stoy, Tuchomefice (CZ); Pavel Vesely, Prague (CZ)

(73) Assignee: MEDICEM TISSUE (CY) LIMITED, Limassol (CY)

( * ) Notice: Subject to any disclaimer, the term of this patent is extended or adjusted under 35 U.S.C. 154(b) by 654 days.

(21) Appl. No.: 12/738,551

(22) PCT Filed: Oct. 17, 2008

(86) PCT No.: PCT/CZ2008/000128
§ 371 (c)(1),
(2), (4) Date: Jul. 9, 2010

(87) PCT Pub. No.: WO2009/049568
PCT Pub. Date: Apr. 23, 2009

(65) Prior Publication Data
US 2010/0291172 A1 Nov. 18, 2010

(30) Foreign Application Priority Data
Oct. 17, 2007 (CZ) .................................... 2007-725

(51) Int. Cl.
| | | |
|---|---|---|
| *A61K 38/39* | (2006.01) | |
| *A61L 27/50* | (2006.01) | |
| *A61L 27/60* | (2006.01) | |
| *A61L 27/36* | (2006.01) | |
| *A61L 27/38* | (2006.01) | |

(52) U.S. Cl.
CPC ............ *A61K 38/39* (2013.01); *A61L 27/3633* (2013.01); *A61L 27/3691* (2013.01); *A61L 27/38* (2013.01); *A61L 27/3813* (2013.01); *A61L 27/50* (2013.01); *A61L 27/60* (2013.01); *A61L 2430/40* (2013.01)

(58) Field of Classification Search
CPC ....... A61K 38/39; A61L 27/50; A61L 27/38; A61L 27/3633; A61L 27/3691; A61L 27/60; A61L 27/3813; A61L 2430/40
See application file for complete search history.

(56) References Cited

U.S. PATENT DOCUMENTS

| | | | |
|---|---|---|---|
| 4,801,299 A * | 1/1989 | Brendel et al. .............. 623/1.47 |
| 5,141,747 A * | 8/1992 | Scholz ........................... 424/424 |
| 6,358,284 B1 * | 3/2002 | Fearnot et al. ............. 623/23.72 |
| 2002/0085994 A1* | 7/2002 | Ceres et al. ................. 424/93.7 |
| 2006/0159664 A1* | 7/2006 | Pandit et al. ................. 424/93.7 |
| 2007/0003603 A1* | 1/2007 | Karandikar et al. .......... 424/443 |
| 2008/0091235 A1* | 4/2008 | Sirota ........................... 606/215 |
| 2009/0226541 A1* | 9/2009 | Scholz ................ A61K 9/0034 424/672 |

FOREIGN PATENT DOCUMENTS

WO WO 2005097219 A2 * 10/2005 ......... A61L 27/3633

OTHER PUBLICATIONS

Leikina et al. Type I collagen is thermally unstable at body temperature. PNAS 2002. vol. 99, No. 3, p. 1314-1318.*

* cited by examiner

Primary Examiner — Taeyoon Kim
(74) Attorney, Agent, or Firm — Fox Rothschild LLP; Gerard P. Norton; Michael S. Montgomery

(57) ABSTRACT

The subject of the invention is a sterile, dehydrated acellular implant, which during its rehydration by water or bodily fluids displays anisotropic expansion and can act as a substrate for adhesion, migration and growth of live cells. Collagen structures of the transplant are at least partially denatured through the action of heat or organic solvents, such as lower aliphatic alcohols and ketones, which simultaneously act as preservative and sterilization agents, especially for certain types of viruses. The implant is sterilized by radiation while in an substantially dehydrated state, preferably by accelerated electrons. The transplant can be derived from various animal tissues, especially mammalian tissues, such as human or porcine tissues. The tissues suitable for the invention can be, for example, skin, placenta, pericardium, peritoneum, intestinal wall, tendon, blood vessel, etc. The implant is suitable for use in human and veterinary medicine, for instance as a temporary wound and burn cover, for the repair, substitution and regeneration of tissues, and also as a substrate for laboratory cell cultivation.

16 Claims, 8 Drawing Sheets

Conformation and adhesion of the cover to the wound without outer dressing $2^{nd}$ degree burn after healing and the self-detachment of the cover Recombined skin with human keratinocytes cultured in an immersion on a porcine acellular matrix according to the invention Recombined skin with human keratinocytes cultured on the interface of air and porcine acellular matrix according to the invention.

STERILE AUTOLOGOUS, ALLOGENIC OR XENOGENIC IMPLANT AND THE METHOD OF ITS PRODUCTION

FIELD OF THE INVENTION

The invention relates to wound healing and tissue regeneration. Specifically it concerns a sterile dehydrated acellular implant (transplant), which during its rehydration by water or bodily fluids displays anisotropic expansion. Product of this type can be called either an implant or a transplant, depending on context and custom in various areas of expertise. In the present application, both terms are used according to the context, however, it is important to keep in mind that they are mutually interchangeable. The implant is sterilized using radiation while in an essentially dehydrated state, preferably using accelerated electrons. The implant can derive from various animal tissues, especially from mammalian tissues, such as for example human or porcine tissues, such as, for example, skin, placenta, pericardium, peritoneum, intestinal wall, tendon, blood vessel, et cetera. The implant, according the invention, is suitable for use in human and veterinary medicine, for example as a temporary wound and burn dressing, for the repair, substitution, or regeneration of tissues, and as a substrate for laboratory cell cultivation.

BACKGROUND OF THE INVENTION

Tissues and organs have long been commonly transplanted for a number of indications. One of the well-established techniques is autotransplantation, where the patient's own tissue (eg. skin, bone, vein, or fat tissue) from one location is used to replace the tissue in another place. This is not always possible, however, and in a number of situations the patient needs to receive a transplant (eg. heart, kidney, retina, and others) from a suitable donor. The main problems of these so-called allotransplants are tissue rejection, and increasingly, lack of donors due to highly increasing demand. Therefore there is an effort to substitute natural allotransplants in various ways. For example, it is possible to culture autotransplants from the patient's cells using tissue engineering. These autotransplants easily overcome the immunity barrier, however they have certain disadvantages: the necessity to harvest tissue from the patient (biopsy), laborious and expensive cultivation and a long time lapse between biopsy and the transplant's application. This technique is commonly used when replacing skin in case of burns of $3^{rd}$ degree, while in case of other tissues and organs, this technique is, at this point, experimental. For example, U.S. Pat. Nos. 6,878,383; 6,432,710; 5,858,390; 5,665,372 and 5,660,850 (Boss, Jr. et al.) describe techniques and means for the implantation of autologous fibroblasts in order to produce hyperplasia of patient's tissue.

Autotransplantation using artificially created epidermal skin layer has been used in burn patients for a number of years. In the year 1979, Rheinwald and Green (Green H, et al., Proc. Nat. Acad. Sci. USA, 1979; 76: 5665-8.) developed a method for the serial cultivation of human keratinocytes for autotransplantation. Since 1981, autologous cultivated epidermal grafts have been used in the USA for the healing of extensive burns (O'Connor N E, et al., Lancet 1981; 1: 75-8). The disadvantage of the method is the long time interval necessary for the cultivation of autologous keratinocytes, furthermore the fragility of the cultivate, difficult manipulation, high sensitivity to antibiotics, infection and other stresses and difficult evaluation of the assimilation of the graft (Navsaria H A, et al., Trends in Biotechnology 1995; 15: 91-100). Various improvements of the method are therefore described, such as:

U.S. Pat. No. 4,299,816 (M. G. Eisinger) describes modified healing of burns using grafts from artificially cultivated epidermal cells. U.S. Pat. No. 5,716,411 (Orgill et al) describes a healing method leading to skin regeneration for burns and injuries, using a biosynthetic cover consisting of a collagen matrix and glycoaminoglycanes, which allows the penetration of cells and blood vessels from the healing tissue on one side, and the application of sheets of autologous keratinocytes on the other side. WO 2006/107188 A1 (L. Lurvink et al.) describes a non-porous polypeptide film suitable for cell cultivation, and its subsequent use for the healing of wounds and burns. A recent overview of these methods can be found in TISSUE ENGINEERING Vol. 12, No. 9, 2006 Update on Tissue-Engineered Biological Dressings, M. Ehrenreich and Z. Ruszczak.

Not only autologous, but also allogenic cultivated epidermal grafts have a high healing effect in deep dermal burns, biopsy sites, crural ulcers and other skin defects (Bolivar-Flores J, et al., Burns 1990; 16: 3-8.; Matouskova E. et at., Burns 1993; 19: 118-23.4, 5).

The success of the procedure depends also on the selection of donor cells. P. Brychta et al. describe in the Czech Patent No. CZ 282711 a cultivated epidermal allotransplant from embryonic or fetal cells for the healing of skin defects and wounds, essentially according to the procedure of Reinwald and Green but while using allogenic cells, which are well received by the patient.

There is also an effort to increase mechanical resistance and viability of keratinocytes (eg. by cultivation on a synthetic substrate) and to develop techniques, which would enable permanent assimilation of the cultivated tissue onto $3^{rd}$ degree burns. One example of a substrate used for the cultivation of keratinocytes is a membrane based on hyaluronic acid (Laser skin, FIBIA, Italy), various types of collagen matrixes combines with fibroblasts or also various substrates made of synthetic polymers (eg. experimental pHEMA at the Clinic of Burn Medicine, FNKV in Prague 10). To fill deep burns, dermal substitutes are developed such as Integra (collagen combined with glucose aminoglycan chondroitin-6-sulphate and allogenic fibroblasts; Integra LifeSciences Corporation, Plainsboro, N.J., USA), Dermagraft (polygalactin seeded with dermal allogenic fibroblasts; Advanced Tissue Sciences, La Jolla, Calif., USA), or the already mentioned AlloDerm—frozen allogenic dermis (LifeCell Corporation, The Woodlands, Tex., USA). However, all these dermal substitutes must be covered by a thin autologous dermo-epidermal graft during the second step (after 2-3 weeks of vascularization), the covering of $3^{rd}$ degree burns using allogenic cultivated was not successful so far.

Another solution to the problems of allotransplantation is the use of tissue or organs from other species other than human, the so-called xenotransplantation. In this case it is also necessary to overcome the rejection of foreign tissue by the immune system, and it is also necessary to prevent the possibility of contamination of disease-causing microbes, germs, and viruses, from the donor to the patient. A great deal of attention is directed to prevent the possibility of transmission of prions from animals to man (eg. the famous "mad cow disease"). On the other hand, the advantage lies in the fact that animal tissues and organs are a lot more accessible than human ones.

A well-known example of xenotransplant is porcine heart valves, used to replace human heart valves. Porcine valves are cross-linked using glutaraldehyde (eg. U.S. Pat. No. 4,076,468, Liotta et al.; U.S. Pat. No. 4,247,292. W. A. Angell), which leads to several desirable results: the rejection reaction of the organism is suppressed, the hydrolytic and enzymatic stability of the xenotransplant is increased, and furthermore, glutaraldehyde acts as a chemical sterilizing agent. One of the disadvantages of this method is the change of mechanical properties of the tissue and in some cases even a long-term release of toxic glutaraldehyde from the insoluble polyaldehydes, which can form during the process and cannot be removed through simple extraction.

A significant portion of transplants is used in the form of so-called "biological covers" for wound dressing and the resultant healing support. Depending on the nature of the wound and other circumstances, biological, synthetic, and semi-synthetic covers are used. Biological covers are generally considered to be the most effective. A typical biological cover for the healing of, for example, burns, is mammalian skin, but especially human skin (allotransplant), or pig skin (xenotransplant) in various thicknesses, harvested from dead individuals and stored fresh under cold temperatures for a short period of time, or for even a longer period of time when frozen. Much experience was derived by xenotransplants from pig skin.

"Live" wound dressings (i.e. unprocessed allotransplants or xenotransplants containing all components of live skin) are very effective, but their disadvantage lies in their limited shelf life and in the possibility of transfer of infection. Certain solutions were suggested in a number of patents, eg. products AlloDerm and XenoDerm by the LifeCell Corp., Texas, USA, based on a cryopreservation method according to U.S. Pat. No. 4,865,871 (S. Livesey et al.). This method enables freezing and possibly freeze-drying tissues and cells without damaging their structure or function.

Another method is the storage of pig skin in glycerine in the presence of silver nitrate at room temperature, as described in the patent application CN 19951010722 (Kai Cao).

Sterilization of pig skin (after being cleaned and processed using hydrocarbons), in a sodium perchlorate or hydrogen peroxide solution using gamma radiation from a $Co^{60}$ source is described in a patent application TW 199001117733 (Chang Hong Chi et al).

Other methods for the sterilization of pig skin for medical use are described in patent application CN 19921005926 (Guohui Li et al.), which describes either sterilization in wet state using a cobalt radiation source, with subsequent cold-temperature storage, or freeze-drying with subsequent storage in glycerine at room temperature.

Conservation using glycerine is also recommended for the human placenta (amnion) used for allotransplants by the Deutches Institut fur Zell- and Gewebeersatz gGmbH (Delitzcher St 141, 04129 Leipzig, SRN).

Document UA 12391U (E. Y. Fistal et al.) describes the healing of necrotic wounds after deep burns using freeze-dried pig skin.

Biological wound dressings based on collagen for the healing of wounds, including burns, are also described in documents RU 2185179 and RU 2124354.

The problem of sterility and shelf life can be attenuated by the removal of cells from the transplant, which will thus become partially or entirely acellular. One effort at solving this problem can be found in the patent document No. CN 20031124306 (Hu Jie), describing xenotransplant as a biological dressing for wounds and burns. Animal tissue, such as skin, small intestine wall or placenta, can be partially rid of cells according to the above invention by using water and detergent solution, and this is done on the surface which will be in contact with the wound. The cellular structure of other parts, such as the epidermis, will remain preserved. Then the tissue will be crosslinked using an appropriate agent, such as glutaraldehyde, will be washed out, and will be stored in wet state at a temperature below 4° C.

Another document, CN 20051126108 (Dong Qun Lin), describes the manner of cell removal from mammalian skin through the repeated action of 2N to 5N NaOH solution, followed by washing in a detergent solution and in water.

Another document, CN20041022506 (Dai Weihua et al.), describes the manner of preparation of a biodegradable acellular dermis using the combined action of enzymes, alkalis, and other chemical agents.

Published application US 20050186286 (Yoshihiro Takami) describes the method of cell removal from mammalian (eg. human or pig) skin using a combined action of proteolytic enzymes and detergents, whereas thus prepared skin is designated for use as an allotransplant or xenotransplant for burns healing. Sterilization is done by a subsequent immersion of the acellular dermis into an azide solution.

Similar acellular xenodermic matrix is OASIS, made by AelsLife, which provides a framework for a three-dimensional migration of cells. This biological wound cover, which according to the manufacturer contains important non-cellular compounds and structures present in live skin, is made by lyophylization of porcine dermis after the cells are removed using enzymes and detergents.

Biosynthetic bandage E*Z DERM, by manufacturer Brennen Medical Inc., uses a porcine dermis xenograft, treated by crosslinking of collagen using aldehydes.

Patent document JP19900247300 (Koide Mikio) describes a biological cover using a denatured collagen matrix, formed from acellular bovine dermis through cross-linking and heat-induced denaturation of collagen structures. This structure is, according to the cited invention, appropriate for seeding using autologous keratinocytes for higher healing efficacy.

Other efforts to resolve the problem were various semi-synthetic skin substitutes, for example a scaffold from a reconstituted bovine collagen, seeded with human fibroblasts (i.e. the above-mentioned INTEGRA dressing.)

Another example of a combined transplant is the "recombined skin: (RK) according to the CZ Patent No. 281176. RK is prepared using cultivation of human keratinocytes on a cell-free porcine-dermis. Burns 1993; 19: 118-23). The dried dermis is used for the cultivation of human keratinocytes and after cultivation the dermis, with a keratinocyte layer (or RK), is detached from the Petri dish and applied to the wound. RK is applied with the keratinocytes in contact with the wound, and the dermis on the outside ("upside down"). As compared to simple epidermal grafts, the RK shows an advantage of higher durability, the detachment from the Petri dish without enzymatic action, and easy manipulation. An advantage as compared to keratinocyte cultures on synthetic substrates and collagen-based gels is that RK's consistency is similar to skin, and this results in excellent wound adhesion and a hemostatic effect. It's possible to make RK using both autologous and allogenic keratinocytes. Keratinocytes are cultured on the epidermal side of epidermis, i.e. where the basal membrane divides the dermis from the epidermis. The inventor of the above cited invention mentions that the cell-free dermis can be sterilized using gamma radiation for better shelf-life at room temperature and higher safety. A disadvantage of thus gamma-sterilized dermis is, however, its partial degradation and loss of durability in wet state.

A similar combined biological burn dressing is described in the patent application TW20000118374 (Yang Mei-Ru et al.), where live human fibroblasts in an acellular porcine dermis are combined with human keratinocytes cultured on the basal-membrane side of an acellular matrix.

A general problem, which prevents a significant acceptance of use of these biological materials, is the fact that it is impossible to use a routine and reliable sterilization process. Another specific problem which prevents wider use of the above-mentioned materials is their limited or demanding shelf-life, and last but not least, their manufacturing cost. A difficult problem is also displayed by dehydrated materials which swell isotropically during rehydration, i.e. the (relatively) equal increase of all of the transplant dimensions after rehydration. The present invention brings a solution to these problems.

SUMMARY OF THE INVENTION

The inventors found that the presence of transplanted allogenic or autogenic cells is not always necessary for wound healing and tissue regeneration, as long as an appropriate material is present which will stimulate, support, and direct the replication, differentiation, and migration of patient's own cells. According to the invention presented herein, this material is a specially processed, acellular collagen matrix derived from an autologous, allogenic, or even xenogenic biological material. According to the invention, the matrix consists mostly of collagen and related proteins, such as elastin, fibrin or keratin. These matrix components and their concentrations change in dependence on the origin of the tissue and its processing method, and for the sake of simplicity will be called "collagen", because in all instances collagen is the main matrix component. Besides proteins ("collagen"), the matrix also contains a certain level of lipids and lipoproteins (up to 20% by weight), a certain amount of sugar components (polysacharides, glycoproteins and glycoproteoglycanes) and salt. The protein content is typically between 70% (by weight) to 95% (by weight), preferably between 80% and 90% (by weight).

According to the invention, the acellular matrix is characterised namely by that it is essentially dehydrated and consists mostly of collagen, whose fibrils display a similar structural organization to the way they were in the original tissue, but in addition they are also partially denatured and, at least in dehydrated state, they are preferentially oriented in a certain selected direction or directions. Partial denaturation is beneficial because it increases resistance to biodegradation, so that the fibrils provide more time for the migration and attachment host's cells during healing. Excessively fast implant degradation can leave behind an inflammatory focus, which will heal with difficulty and can lead to scarring. Partial denaturation of collagen fibrils also increases mechanical strength in wet state.

The orientation of collagen fibrils also gives the implant higher strength in the chosen direction and it directs the migration and dissemination of cells along the surface of the implant, rather than their penetration into the implant. This is further supported by the fact, that the acellular matrix, according to this invention, has low porosity in dehydrated state in comparison with freeze-dried biological wound covers, whose porosity is usually higher than 75% (by volume). According to the invention, the implant's porosity is lower than 70% (by volume), preferably lower than 60% (by volume), and even more preferably lower than 50% (by volume). Low porosity and an advantageous fibril orientation are important especially for implants used as biological wounds covers, for example burns, which are supposed to separate spontaneously once the healing is complete. The regeneration of epidermal layer demands the migration of keratinocytes form the wound's edge to the areas of healing, that being the interface between the wound and the implant's surface. The infiltration of cells into the implant's structure would not be advantageous, because it could lead to the reattachment of the transplant to the wound. When the transplant is subcutaneous, for instance, the migration of cells along its surface will result in the formation of a fine fibrous cyst, which is undesirable in many cases.

The preservation of collagen orientation in dehydrated state also decreases the tangential stiffness of the implant (tangential to the orientation of the fibrils), therefore even a dehydrated implant is easier to bend and less fragile than a similar anisotropic one. This is of significant practical importance, since the dehydrated implant does not need softeners, and cracks and micro-ruptures, which might result in uncontrolled infiltration of cells into the implant, its disintegration, and possible calcification, do not form in it.

Another important result of the anisotropic organization of the collagen fibrils is the anisotropic swelling during implant rehydration. According to the invention, the implant expands at various rates in various directions during rehydration. For example, if the collagen structures are preferentially oriented in the longest direction (eg. when using a tendon), then most of the hydration expansion will be displayed as an increase of the implant's diameter, while the length will change only a little, or can remain the same, slightly increase or even decrease, according the relationship between structural anisotropy and swelling. In case of a surface implant, such as a burn wound cover, the fibril orientation can be selected to run preferably in a perpendicular direction to the surface of the main implant plane. In this case, the hydration expansion will express itself especially or only as the increase of thickness, while the footprint will remain essentially unchanged. The anisotropy of swelling has, aside from above-mentioned advantages, another practical advantage: the surgeon can better adjust the shape and size of the implant to the requirements of the individual patient. For example, if a wound of a particular shape must be covered, an implant of a corresponding size and shape can simply be cut out from the dehydrated implant, and will remain unchanged after hydration. In case of isotropic dehydrated implants the dehydrated dimensions would have to be relatively smaller in order to compensate for the effect of hydration expansion. Another advantage can also be the way the dehydrated implant, affixed to tissue, maintains its shape after hydration and thus the surrounding tissue retains the tension which was selected by the surgeon during surgery. In case of an isotropic implant, the surrounding tissue would lose its original tension as a result of the hydration expansion of the implant.

Significant is also the fact that the anisotropy of the expansion allows for a simple differentiation of the implant according to this invention from other implants of similar origin and purpose.

The anisotropy of swelling can be expressed as a ratio between linear expansion coefficients in three selected dimensions. For instance, a selected direction along the axis "z" can be thickness t and its linear expansion coefficient $C_z=(t_{hydrat.})/(t_{dehydrat.})$. Similarly, we can select length as l as the dimension in the direction of the axis "x" and define the linear expansion coefficient as $C_x=(l_{hydrat.})/(l_{dehydrat.\ u})$. And finally, as the dimension in the direction of axis "y" we can select width w and define the linear expansion coefficient $C_y=(w_{hydrat.})/(w_{dehydrat.})$, where the subscript "hydrat."

means the size (dimension) after hydration and the subscript "dehydrat." means the size (dimension) in the original, dehydrated state. In case of an isotropic dehydrated material we will always find that $C_z/C_y=C_x/C_z=C_y/C_z=1$, no matter what are the values of $C_x$, $C_y$, and $C_z$. Anisotropic expansion during hydration is distinguished by the fact that at least one of the ratios $C_x$, $C_y$, and $C_z$ has a value different from 1, and at least one of the linear expansion coefficients $C_x$, $C_y$, and $C_z$ has a value lower than the others and it's value can even be lower than 1. At least one of the linear expansion coefficients $C_x$, $C_y$, and $C_z$ has, conversely, a value significantly higher than the others, usually by at least 10%, preferably by more than 30%. For instance, the linear expansion coefficients $C_x$, and $C_y$, can have a value lower than 1, while $C_z$ has a value higher than 1.2 and preferably higher than 1.5.

According to this invention, the collagen fibrils of the anisotropic dehydrated implants are oriented preferentially in the direction of the lowest linear expansion coefficient, or as the case may be in a plane perpendicular to the direction, in which the expansion coefficient value is the highest.

Collagen fibrils may be preferentially oriented in a certain direction even in a fully hydrated state. This orientation can be achieved by partial denaturation of collagen in oriented state, or the cross-linking of collagen (which is also a form of denaturation). The orientation of collagen fibrils will then remain essentially maintained even after the implant's hydration. This orientation can be used to an advantage for the direction of migration and proliferation of cells in a certain direction, which is advantageous especially in the healing of burns.

The cross-linking of collagen can be achieved using various well-known methods, for instance the action of aldehydes, such as for example formaldehyde or glutaraldehyde, or polyvalent cations, such as for example, $Ca^{2+}$, $Mg^{2+}$, $Al^{3+}$ or $Cr^{3+}$. Cross-linking will further lower swelling and increase the strength and hydrolytic resistance of the collagen matrix. This ionic cross-linking is, in the implanted state, often unstable and the gradual lowering of cross-linking density will then lead to a gradual increase in swelling and to the change of the linear expansion factors and their mutual ratios. The kinetics of these processes is controllable and therefore these processes can be used, for instance to produce directed pressure or tension on the healing tissues.

According to the invention, acellular matrices are strongly hydrophilic and their volume will increase with hydration. Hydration is most often defined as a weight fraction of water in hydrated state, or as water content in weight %. According to the invention, water content in the fully hydrated implant is higher than 33% (by weight) and preferably higher than 50% (by weight). The coefficient of volume expansion is defined as:

$$C_v=C_x*C_y*C_z=(\text{hydrated volume})/(\text{dehydrated volume})>1.$$

According to the invention, acellular matrices have $C_v>1.1$, preferably $C_v>1.5$. In this they differ, in principle, from substantially hydrophobic porous structures, which can be formed, for example but covalent cross-linking of tissues with the help of, for example, aldehydes, or they can be formed from synthetic polymers, such as for example polyurethanes. In that case, during hydration, water fills pores and increases the mass of the implant, but its volume does not increase appreciably and its $C_v$ is close or essentially equal to 1.

From the information stated above it can be concluded that the subject-matter of the invention is most especially an acellular, sterile, essentially dehydrated and at least partially denatured matrix, derived from an animal tissue and containing mostly collagen, whose fibrils are in a similar structural arrangement as they were in the original tissue, intended as a temporary implant in human or veterinary medicine, and which matrix displays anisotropic changes of its dimensions during hydration.

According to the advantageous embodiment of the invention, during hydration of acellular matrix, when anisotropic changes of matrix dimensions occur, the two largest dimensions remain essentially constant or become smaller, while the smallest dimension increases along with the matrix volume increase.

According to the invention, in another advantageous embodiment the temporary implant has an essentially flat shape, whose footprint is defined by its two largest dimensions, while its thickness is defined by its smallest dimension.

According to the invention, in yet another advantageous embodiment of the acellular matrix, the two of its smaller dimensions will increase, while its largest dimension remains essentially constant or decreases in size.

In yet another advantageous embodiment, the temporary implant has an essentially long shape, such as a prism or a cylinder, whose diameter is defined by its two smallest dimensions, such as for example its diameter, while its length or height is defined by its largest dimension.

According to the invention, an advantageous matrix in a dehydrated state has porosity lower than 70% (by volume), advantageously lower than 60% (by volume), and most advantageously lower than 50% (by volume).

According to the invention, in an advantageous embodiment the acellular matrix consists of collagen fibrils which are, at least in dehydrated state, preferentially oriented in the directions in which the hydration linear expansion coefficient has the lowest value, and basically perpendicularly to the direction, in which the linear expansion coefficient the highest value.

According to the invention, in an advantageous embodiment the acellular matrix, in a dehydrated state, has a water content lower than 20% (by weight), advantageously lower than 10% (by weight) and most advantageously lower than 5% (by weight).

According to the invention, in certain advantageous embodiments the matrix can also contain softening, preserving, or bactericidal additives. Advantageous bactericidal additives contain silver, preferably in colloidal state and even more preferably as a silver-protein complex. Advantageous softening or preserving additives contain compounds miscible with water, such as DMSO or polyhydroxy compounds selected from the glycol or glycerine families or their derivatives, triethanolamine, and sacharides.

According to the invention, an advantageous acellular matrix is capable of volume expansion in contact with aqueous liquids, with a volume expansion factor higher that 1.1, preferably higher than 1.5. Furthermore, an advantageous acellular matrix, once exposed to suitable aqueous solutions, is capable of assuming a form where it contains more than 33% water (by weight), preferably more than 50% water (by weight).

According to the invention, an advantageous acellular matrix has the highest linear expansion coefficient 10% higher, preferably 30% higher, than the lowest linear expansion coefficient. Preferable are acellular matrices whose highest linear expansion coefficient have a value higher than 1.2, preferably higher than 1.5, while the lowest linear expansion coefficient have a value lower than 1.1, preferably lower than 1.05.

According to the invention, in another advantageous embodiment, the solids (dry matter) of the acellular matrix consist predominantly of proteins, where the preferred protein contains predominantly collagen. Even more preferably, the solids (dry matter) of an acellular matrix contains 70% (by weight) to 95% (by weight), advantageously 80% (by weight) to 90% (by weight) collagen-type proteins. Advantageously the solids (dry matter) of the matrix contain, aside from proteins, a lower fraction of lipid compounds including lipoproteins and phospholipids.

According to the invention, the acellular matrix is advantageous when its protein fraction is at least partially denatured. According to the invention, in another embodiment at least the protein fraction of the acellular matrix is cross-linked as a result of a reaction with aldehydes or polyvalent cations.

According to the invention, an advantageous acellular matrix is derived from a mammal, preferably from a pig.

According to the invention, an advantageous animal tissue for the acellular matrix is skin, placenta, pericard, dura mater, intestine, tendon, or cartilage.

The temporary implant formed by the acellular matrix as claimed in the present invention, is advantageously used as a wound cover, most advantageously as a burn cover.

According to the invention, another advantageous embodiment of the acellular matrix is one which also contains cultured mammalian cells. Preferably the mammal is a pig and the cultured mammalian cells are human autologous or allogenic keratinocytes.

According to the invention, another advantageous embodiment of the acellular matrix is one which will biodegrade spontaneously after its function is fulfilled.

The manufacturing method of the implant according to the invention, as was described above, includes several basic steps:

1) Implant harvesting, such as of porcine skin or human tendon. This step is done basically in the same way as in the case of other, up to now common harvestings, but with the important advantage, that according to the invention the implant harvest is not as demanding as to transport conditions and subsequent rapid processing as it would be in case of implants containing cells. Collagen structures, which will become the final implant, are more stable than cellular structures.

2) Cell removal. According to the invention, various methods of cell removal can be used for this implant, including methods described in the current state of technology. This includes cell removal by surfactants, such as detergents, chemical compounds such as acids and alkalis, or enzymes, as described in subsequent patent applications and documents, which are hereby included in the present application CN200310124306 (Hu Jie); CN20051126108 (Dong Qun Lin); CN20041022506 20040512 (Dai Weihua et al.); US 2005 0186286 A1 (Yoshihiro Takami); JP 19900247300 (Koide Mikio) and CZ Patent No. 281176 (E. Matouskova).

According to the invention, a two-step method is advantageous, where in the first step the harvested tissue is exposed to a suitable proteolytic enzyme, such as trypsin or papain, and in the second step the tissue, including potential remaining cells, is exposed to a strong hypotonic solution, preferentially to an excess of distilled or deionized water. Deionized water will remove remaining cells by exposing them to osmotic shock, which will cause a rupture of their membranes. This second cell-removal step occurs together with a multi-step extraction of remaining enzyme (such as trypsin) and other compounds. Along with the removal of remaining enzyme, soluble peptides are also removed, as well as polysacharides, glycoproteins, and other compounds with assumed biological activity. The removal of water-soluble compounds is even more effective, since the hypotonic solution causes high swelling of the tissue, thus improving diffusion of the extracts. We found, however, that even a thorough extraction does not remove these water-soluble compounds entirely, and new organic compounds can be detected using UV spectroscopy at the end of each step. This shows that new compounds, such as polypeptides and glycoproteins, keep being released from the collagen structure, therefore a certain level of biological activity remains preserved.

3. Dehydration. Dehydration is done by the removal of at least the substantial fraction of water either using evaporation of water present in the acellular structure, or its extraction using a suitable solvent, such as ethanol. "Substantial fraction of water" here is meant to be the so-called "free water", which is the fraction of water, whose structure and thermodynamic properties are entirely like those of liquid water (for example, melting point, vapor pressure or heat capacity). This is usually most of the water in the tissue, except for the last 20% or so by weight, which consist of water more or less bound into the collagen matrix or into other hydrophilic components of the implant. This so-called "bound water" has other thermodynamic properties than free water and functions as a plasticizer of collagen. It is difficult to remove bound water entirely. "Dehydrated implant" is meant to be an implant which contains no free water, and has a remaining moisture content below 20% (by weight), preferably under 10% (by weight). For increased shelf-life of the product it is especially advantageous to maintain product moisture content below 5% (by weight). If an extraction using a water-miscible solvent is performed, this step already leads to a simultaneous partial denaturation of collagen. In order for the partial denaturation to be effective, toward the end of water extraction the solvent should contain more than 50% of the organic compound by weight, preferably more than 70% by weight. Water extraction can be done in several steps, with gradually increasing concentration of the organic solvent. Suitable solvents are lower aliphatic alcohols $C_1$ to $C_4$, lower aliphatic ketones such as acetone, ethers such as dimethyl ether, diethyl ether, dioxane or tetrahydrofurane, glycols such as ethylene glycol, 1,2-propylene glycol, diethylene glycol or triethylene glycol, and so on. Most suitable is ethylalcohol, which is not only an effective denaturing agent for collagen and other proteins, but also a preservative and sterilization agent, effective even against, for example, retroviruses. Its advantage is also its relatively low toxicity, availability, and the possibility to entirely remove its remnants using evaporation. If the chosen solvent is not volatile, it will be removed using extraction by a volatile solvent such as methanol, ethanol, acetone, or water.

4. Partial denaturation of collagen. The denaturation is done either using heat or through suitable organic agents, such as for instance, alcohols, aldehydes, ketones or their suitable combination. It is also possible to induce denaturation through partial cross-linking of collagen, such as by using polyvalent cations such as $Ca^{2+}$, $Mg^{2+}$, $Al^{3+}$ or $Cr^{3+}$. Cross-linking can improve resistance against biodegradation and thus can lengthen the effective use of the implant.

Partial denaturation of biological covers by heat treatment, cross-linking or their combination is described in the following documents, which are hereby included in the present application: JP19900247300 (Koide Mikio) and U.S. Pat. No. 4,076,468 (Loiotta et al.); U.S. Pat. No. 4,247,292 (W. A. Angell).

Denaturation of collagen can be advantageously done in combination with dehydration, however both steps can also be done separately in whatever order. One advantageous method is dehydration by water evaporation with a subsequent denaturation in dehydrated state, for instance using heat treatment. Denaturation by organic solvent can be done even by sprinkling or spraying a suitable organic agent on the dehydrated implant. Denaturation by solvents can be combined even with heat denaturation by controlled heating of the implant, for example while evaporating water or solvents.

It is important to perform the dehydration and denaturation of the acellular matrix under mechanical tension in one or two chosen directions, usually in the direction of the largest dimensions. Tension during dehydration and denaturation can be achieved by maintaining constant dimension in desirable directions. This can be achieved, for instance, by affixing the acellular matrix with clamps, by stretching it using elastic attachments or rollers, by attachment to a suitable frame, by pressing to an adhesive substrate or by using suction to attach to a substrate using a vacuum, and so on. Dehydration and denaturation in a stretched state will cause the orientation of collagen structures in the direction, in which the acellular collagen matrix is stretched (or in which its contraction is at least prevented during dehydration and denaturation).

If the denaturation is done on an already dehydrated anisotropic matrix, then it is usually no longer necessary to keep it under tension, therefore the dehydrated matrix is dimensionally stabilized up to a certain temperature, which may not be exceeded during manufacturing or storage. This temperature limit is primarily dependent on remaining water content in the matrix, which should not exceed 20% (by weight), preferably 10% (by weight), and most preferably 5% (by weight), relative to the overall mass of the matrix. Denaturation is done between the temperatures of +15° C. and 90° C., preferably between 30° C. and 70° C.

5) Sterilization by ionizing radiation. If the denaturation in step 4 is done using suitable solvents, such as ethanol, we have two levels of sterilization. First level of sterilization during the production process will first of all lower the microbial load for the final sterilization, and secondly it will remove even those germs, against which the second sterilization level may not be effective (eg. retroviruses).

The final sterilization level is done by packaging in a wrapper impermeable to microorganisms and viruses, using radiation. Advantageously a minimal level of ionizing radiation is used for a given microbial load, which will decrease product degradation. The recommended level is lower than 50 kGray, preferably lower than 30 kGray. This is important especially in case of gamma radiation. Preference is generally given to sterilization by accelerated electrons (electron beam, beta radiation), which is gentler to the implant material and can be dosed more accurately. It is important to recognize the differences in the mechanism of degradation for gamma radiation and for accelerated electrons. The originators of the present invention were surprised to learn that the implants sterilized by a combination of ionizing radiation, especially by accelerated electrons together with chemical sterilization agents which simultaneously cause denaturation, especially ethanol, maintain their excellent mechanical properties when wet and are not cytotoxic even when in contact with the cells of the patient or with cells cultivated on the implant in the laboratory. Without regard for various theories the inventors assume that the beneficial effect of ionizing radiation, such as accelerated electrons, is caused primarily by the release of water-soluble peptide and proteoglycane fragments from otherwise insoluble matrix, which allows for its increased biological activity.

The implant can be also combined with known bactericidal or bacteriostatic agents, such as sulphonamides, antibiotics, protein-silver complexes or colloidal silver spread through the collagen matrix. This is advantageous especially during implantation into infected or necrotic wounds. Some additives simultaneously act as softeners, such as glycerine and its diacetate or formaldehyde, 1,2-propylene glycol, diethylene glycol, glucose, triethanolamine or dimethylsulfoxide (DMSO). These may act simultaneously as mild preservatives, softeners and weak denaturing agents. Their content can be up to 50% (by weight), preferably lower than 30% (by weight). These softening additives are miscible with water, and preferably will be polyhydroxy compounds, most preferably glycerine or its derivatives. They can even be used in combination with silver compounds, as described, for instance, in application CN199551010722 (Kai Cao), which is hereby included in this application.

The subject-matter of the presented invention is thus the manufacturing method of an acellular, sterile, essentially dehydrated matrix and at least partially denatured matrix derived from animal tissue and containing predominantly collagen structures, which was already defined above, which is based on the animal tissue being processed using a method comprising the following steps:

a) tissue harvesting
b) removal of cells through enzymatic action, surfactants, acids, alkalis, hypotonic aqueous solutions or their combinations, during the formation of the acellular matrix.
c) dehydration of acellular matrix through the removal of a substantial portion of water, while the matrix is held under mechanical tension in one or more selected directions;
d) partial denaturation of collagen structures in the acellular matrix through the action of increased temperature, organic compounds, polyvalent cations or of their combinations, while the matrix is kept under mechanical tension in one or more selected directions; or the dimensions of the matrix are being kept essentially constant;
e) sterilization of the essentially dehydrated and at least partially denatured matrix by ionizing radiation.

According to the invention an advantageous method of manufacture of the sterile acellular matrix is one where the partial denaturation of collagen structures of the matrix is done using organic compounds miscible with water, selected from the group including aliphatic alcohols $C_1$ through $C_4$, aliphatic aldehydes including formaldehyde and glutaraldehyde, aliphatic ketones including acetone and ethers including dimethyl ether, diethyl ether, dioxane and tetrahydrofurane.

According to the invention, an advantageous way of performing the partial denaturation of collagen structures is under the temperatures 15° C. to 90° C., preferably under 30° C. to 70° C.

The inventors found and verified that the implant according to the invention can be advantageously used as a biological cover for burns, crural sores, harvesting areas and other skin defects. Dehydrated implant can be placed directly onto the bleeding or seeping wound, which will hydrate the implant in situ without a significant increase of the wound cover area and will contribute to the reduction of wound bleeding and seeping. For this use are especially suitable implants softened by suitable additives, such as glycerine. The sterile implant can be also hydrated before use in a sterile physiological solution, possibly with the addition of appropriate bactericidal agents (such as furantoin, boric acid solution or a proteinaceous silver solution in water (a silver-protein complex)), and placed onto the wound. Its great advantage is its ability to closely cover the topographical features of the wounded surface, lowers wound pain and has a hemostatic effect. Another great advantage is the fact that the healing of the whole area occurs without any change of wound dressings, which is necessary in case of other wound dressings, is often expensive and is especially traumatic for the patient (in case of severe burns it even has to be done under full anesthesia). Another advantage in comparison to other biological covers is the fact that it doesn't matter which side is in contact with the wound. The acellular dermal cover protects the wound and accelerates healing by supporting biological activity connected to healing, such as the migration and proliferation of patient's keratinocytes. Native keratinocytes will adhere to the inner surface of the implant (possibly to the fibrine created on the implant after contact with blood or plasma of the patient) and they migrate on its surface, so the implant becomes part of the skin for the period of time when active healing is taking place. As soon as healing is complete and the epidermal skin layer of the patient is renewed, the implant will dry out and it will detach itself spontaneously, without any need for surgical removal, which is necessary for some other biological covers and which is also traumatic for the patient.

Another advantage of the sterile acellular implant, according to the invention, is its suitability as an excellent substrate for cell cultivation, whether autologous or allogenic. Its surface can therefore be used to cultivate suitable cells, such as keratinocytes, which will form a cellular biological cover known as "recombined skin" (RK), which can be applied to burns and other wounded areas. The main advantage of this cellular biological cover is it's ability to combine the stimulatory effect of cultured keratinocytes with the properties of the membrane substrate, that being the implant according to the invention. If the prevention of deepening of deep dermal burns is successful by applying RK within 10 days after the injury, transplant is not necessary, healing will be significantly accelerated, and harvesting areas and surgery repetition will be spared. RK together with transplanted allogenic keratinocytes will temporarily adhere during healing, keratinocytes will be incorporated into the regenerating epidermis, will proliferated, migrate, close the wound and stimulate healing by producing various growth factors. Xenodermis will protect the wound and will provide a natural substrate for the migration of autologous keratinocytes. In the course of one week the allogenic keratinocytes replaced by own keratinocytes. The present invention will be further explained by the following examples and attached figures. These examples serve as a demonstration of certain advantageous embodiments of the invention and the person skilled in the art will certainly see that the scope of the attached patent claims is not limited by the inclusion of these examples to these examples alone.

EXAMPLES

Example 1

Porcine Skin as a Xenotransplant

Figure 1:
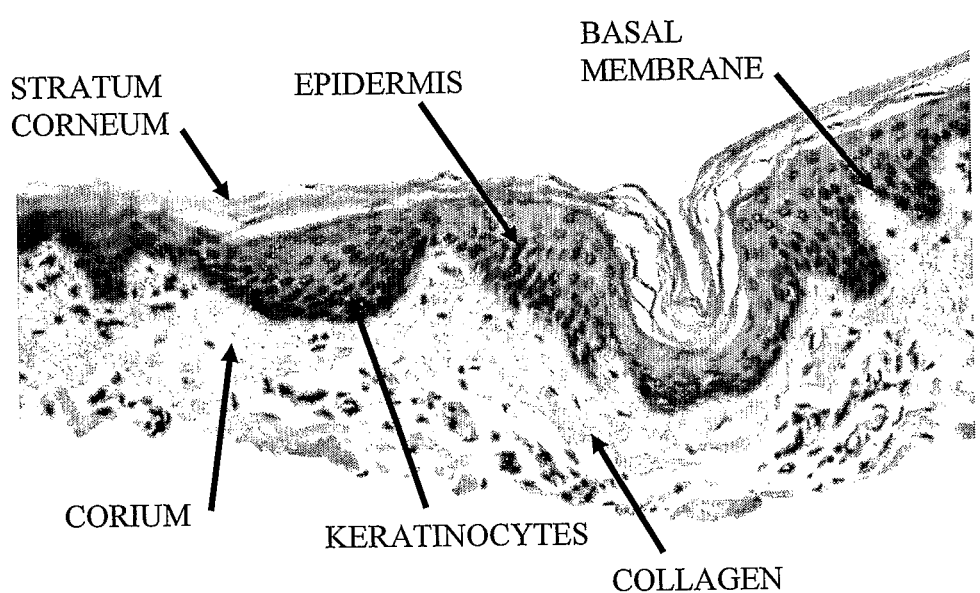
FIG. 1 is a micrograph showing a histological section through porcine epidermis with a papillary corium level.
Figure 2:
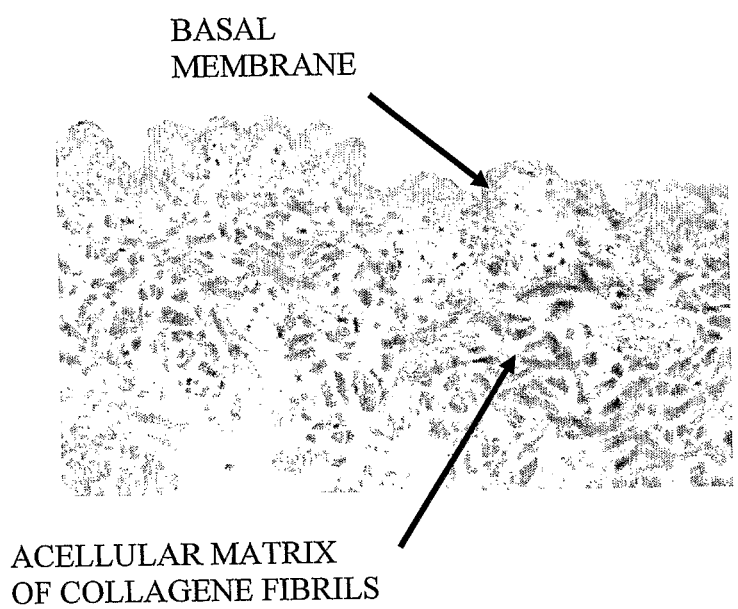
FIG. 2 is a micrograph of a histological section of the implant after cell removal.

Using a dermatome, a 300-400 micron thick layer was cut from a shaved and cleaned porcine epidermis including the papillary corium layer. Histogram of the removed layer is in FIG. 1. The removed strip of porcine skin was immersed 3 times for 20 minutes at 37° C. and the for 12 hours at 4° C. in a 0.25% trypsin solution, which removed most dermal cells and separated the epidermis. The obtained epidermis was washed 6 times in demineralized water (3× for 1 hour, 1× or 12 hours, 2× for 0.5 hours) to remove remaining cells and trypsin. The FIG. 2 histogram shows, that the non-cellular structure was retained. The strip of dermis was then attached with an adhesive to a glass Petri dish and dried at room temperature to constant weight. In this state the dermis contained approx. 18% water. Thus dried acellular dermis had the same footprint area s the original hydrated dermis, but its thickness was less than half. The stretched acellular dermis was then immersed in 96% ethanol at 15° C. for a period of 24 hours. Then the ethanol was decanted and the dermis was detached from its glass substrate, was attached in clamps from two opposite directions, and dried at a temperature of 50° C. for 1 hour.

Figure 3:
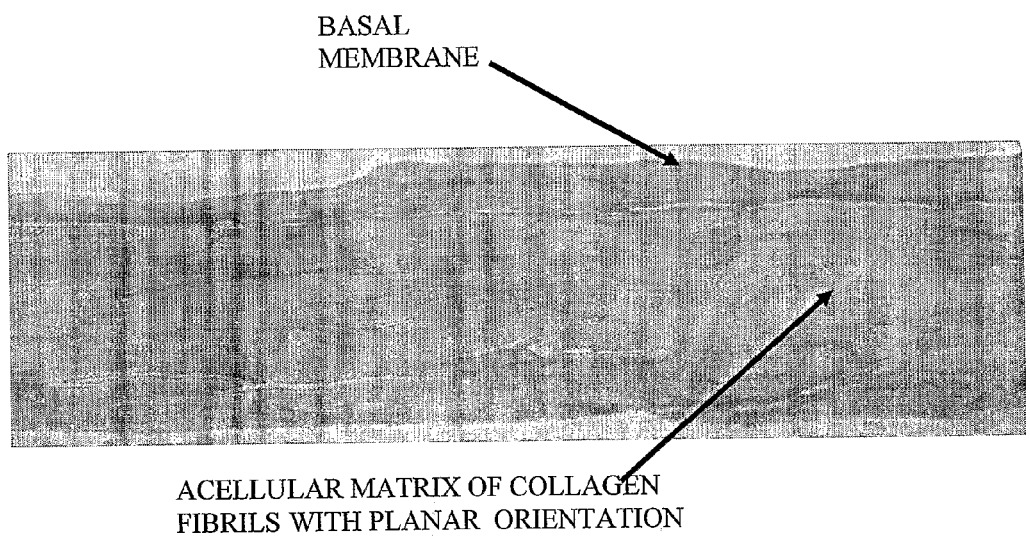
FIG. 3 is a micrograph showing a histological section from a plane-oriented sterile implant after dehydration.
Figure 4:
FIG. 4 is a micrograph showing the staining of collagen structures according to Van Gieson in a histological section of a sterile rehydrated implant according to the invention, magnification 400×.

The dehydrated acellular xenotransplant, containing remaining 9.5% water by weight, was then placed in a sterilization pouch approved for radiation sterilization, was heat-sealed within it, and exposed to a dose of 25 kGy of gamma radiation. Sterility was confirmed using a standard sterility test. After rehydration, a histological section was harvested. FIG. 3 shows that the fibrous structure of the connective tissue is preserved, but it is more compact and the fibers are oriented in a plane. Van Gieson staining on FIG. 4 show's, that the implant consists mostly of collagen-type polymers, such a collagen and elastin. Analysis showed that the implant contains approximately 85% (by weight) mixture of mostly collagen with a smaller amount of elastin and fibrin, where the remainder is composed of lipids, polysacharides, and glycoproteins.

The sterile implant's porosity was around 55% by volume, calculated using density in dehydrated state. The implant was rehydrated at 35° C. in an isotonic NaCl solution. After rehydration to constant mass, water content was 62% (by weight). Repeated measurements of dimensions in both dehydrated and hydrated state were taken with accuracy to 0.01 mm, and the following linear expansion coefficients were found:

Length: $C_x=1.02\pm0.01$
Width: $C_y=1.03\pm0.03$
Thickness: $C_z=1.54\pm0.29$
Planar expansion coefficient: $C_a=1.05\pm0.03$
Volume expansion coefficient: $C_v=1.63\pm0.20$ Obvious differences in expansion coefficients clearly prove anisotropic expansion during implant's rehydration. This anisotropy can be further demonstrated by the values of the ratios of linear expansion coefficients:

$C_x/C_y$ 0.98
$C_z/C_x$ 1.52
$C_z/C_y$ 1.49

Figure 5:
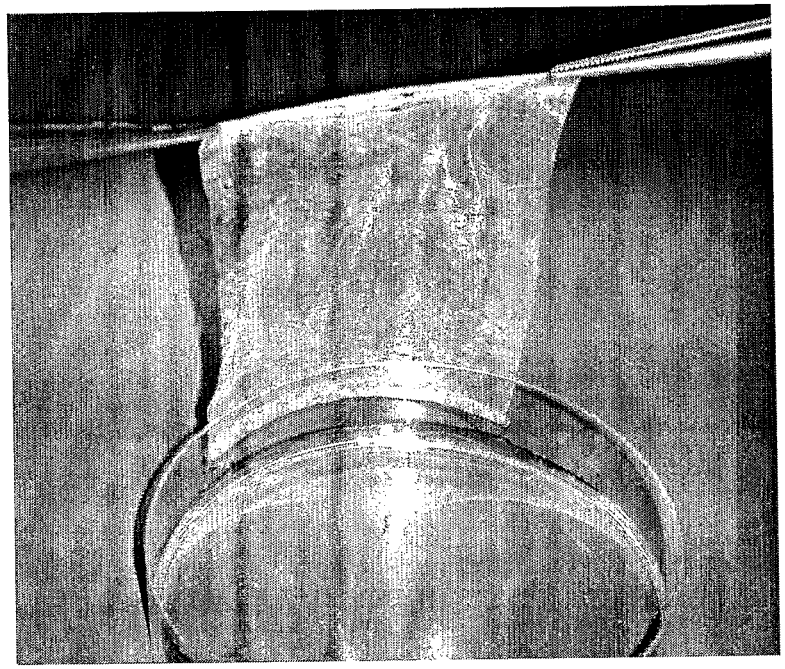
FIG. 5 shows a rehydrated sterile implant prepared for use as a burn cover.
Figure 6:
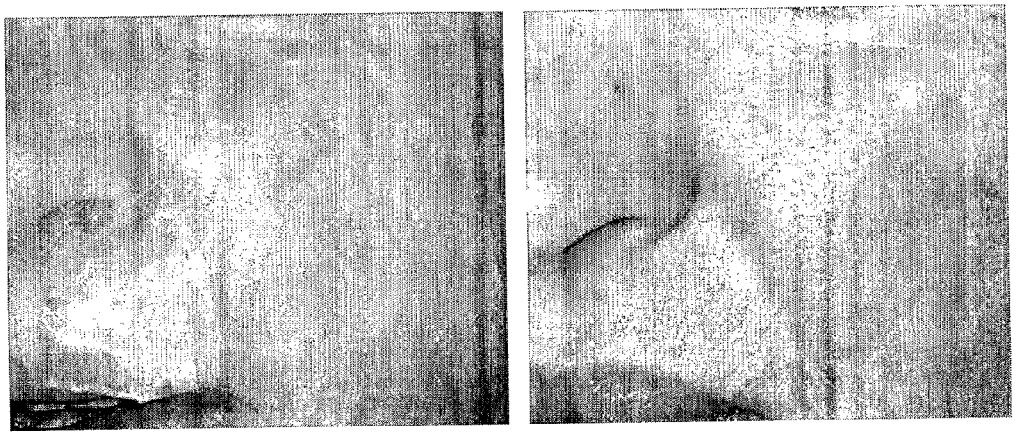
FIG. 6 demonstrates the application of the implant according to the invention on a $2^{nd}$ degree burn: Left photo: conformation and adhesion of the cover to the wound without outer bandages Right photo: $2^{nd}$ degree burn after healing and the self-detachment of the cover.

After a certain storage period the xenotransplant was used as a cover for a deep $2^{nd}$ degree burn on the face. The implant was briefly immersed in a sterile physiologic solution, as demonstrated on FIG. 5, upon which it softened and become supple without any change of the footprint area. It was then placed on the burn, to which it adhered well, as is evident in the left part of FIG. 6. During the healing of the burn the implant stayed in its original place according to the invention, it began to gradually dry out, and after almost one week it began to detach itself from the healed tissue. After 11 days the wound was healed and the cover was detached entirely, as demonstrated on the right side of FIG. 6.

Example 2

Implant Prepared According to Example 1 was Used on a $3^{rd}$ Degree Burn

Figure 7:
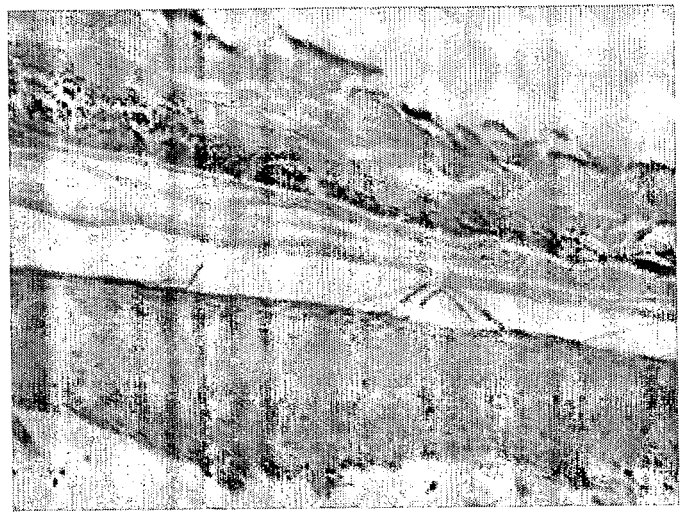
FIG. 7 is a micrograph showing a histological section from the samples of newly formed tissue on a non-necrotic $3^{rd}$ degree burn under the cover made of the implant according to the invention (9 days after application).

The damaged tissue was carefully cut off. The dehydrated transplant was removed from its sterile packaging, was adjusted to the size and shape of the treated area using scissors, was placed on the bleeding wounded area, and was sprayed with a sterile antibiotic solution. The xenotransplant softened quickly and adhered to the wounded area's surface, which stopped the bleeding. The implant retained its dehydrated state footprint, but its thickness increased upon hydration. This caused a perfect conformance to the wound. The implant was covered with a protective layer of tulle gras dressing for the first 3 days. After 8 days the implant dried out to a scab-like consistency and began to separate from the newly formed skin under the cover. New epidermis began to slowly form under the implant, as shown on FIG. 7. After healing was complete, healthy and naturally structured skin was formed, including natural pigmentation, and free of scarring.

Example 3

Human Cartilage as an Allotransplant

Cartilage harvested from a hip joint of a deceased donor was made free of cells by repeated soaking in a trypsin solution and in distilled water, then it was attached, using vacuum, with its concave side onto the convex side of a suitably shaped porous substrate made of fritted glass. While on this substrate, it was placed into an excess of a solution of 20 parts (by weight) methanol and 5 parts (by weight) dimethylsulfoxide (DMSO) at 35° C. for a period of 48 hours. Thus the acellular implant was dehydrated, and at the same time the collagen contained within it was partially denatured in a plane-oriented state. After this period the acellular allotransplant was removed from the solution and methanol was evaporated at room temperature using air stream. At the end of this step the transplant contained approx. 13% (by weight) DMSO, approx. 4% (by weight) water and less that 0.5% (by weight) methanol. After being removed from the porous substrate, the transplant was placed in a waterproof sterilization sack and sterilized using a 45 kGy beta radiation dose from an electron accelerator. Sterility was ascertained using a standard sterility test.

Thus prepared implant is suitable as an experimental replacement of cartilage of the hip joint in dogs, where it is slipped onto the damaged cartilage and attached using a loop of chirurgical suture material around the neck of the head. The implant will hydrate in situ without any change of its footprint, so for the whole period it remains in a stable position relative to the joint of the patient. The implant protects the cartilage against fusion and thus against permanent loss of mobility. Furthermore, the implant supports and accelerates the healing of the cartilage. When healing is finished, the implant gradually degrades and is reabsorbed, until the natural cartilage is healed and the joint function is renewed.

Example 4

Porcine Skin as Matrix for the Cultivation of Keratinocytes (for the Preparation of Recombined Skin)

Figure 8:
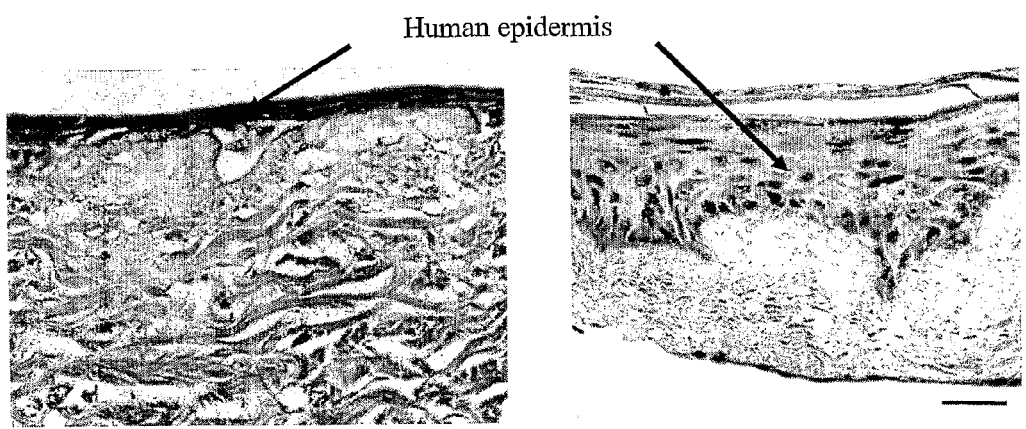
FIG. 8 demonstrates micrographs of histological preparations of recombined skin (RK) formed by lab cultivated human keratinocytes on the implant according to invention Left photo: Recombined skin with human keratinocytes cultured in an immersion on a porcine acellular matrix according to the invention Right photo: Recombined skin with human keratinocytes cultured on the interface of air and porcine acellular matrix according to the invention.

Sterile acellular matrix from Example 1 was removed from its sterile packaging, placed onto a Petri dish used for cell culture cultivation, and carefully inundated with a small excess of distilled water. The acellular xenodermis hydrated without a change of its footprint, only its thickness was approximately doubled as a result of hydration. The excess of water was then carefully aspirated to prevent any deformation of the hydrated dermis, and rest of the water was allowed to evaporate in a laminar flow hood at room temperature. The dried acellular xenodermis was then used for the cultivation of human keratinocytes on lethally irradiated 3T3 fibroblasts (they do not replicated, but they metabolize and produce important growth factors), which created the so-called recombined skin (RK), containing allogenic keratinocytes cultivated on xenogenic acellular dermis according to the invention. The structure of the keratinocyte layer was determined by cultivation conditions, as is apparent from FIG. 8. When the cultivation was done on the implant's surface under immersion, a smooth, regular keratinocyte layer resulted. When the cultivation was done on an implant/air interface, the keratinocyte layer structured itself into a form similar to natural epidermis, including the horny layer stratum corneum, and the basal membrane, stratum basale. Thus prepared RK can be used for the healing of burns, crural sores, and other hard to heal skin defects.

RK is applied with the keratinocytes facing the wound and the dermis outside ("upside down"). According to the invention, the xenodermis, which serves as a cultivation substrate during the cultivation phase, serves as a support structure for the keratinocyte transfer during the graft's application; it protects the wound from infection, drying and mechanical damage. The advantage as compared to simple cultivated grafts is higher resistance, a release from the Petri dish without enzymatic action (using only 2 tweezers), and easy manipulation. An advantage as compared to keratinocyte cultures on collagen-based gels is RK's consistency, which is similar to ordinary skin, and the resultant excellent adhesion to the wound and also a hemostatic effect. When released from the Petri dish the graft does not contract, the keratinocytes on the substrate are not affected during release like they would be by enzymes. RK with allogenic keratinocytes has stimulating effects on the healing of graft harvesting areas and for the healing of deep dermal burns ($2^{nd}$ degree).

The main advantage of this cell biological cover is its combination of stimulation effects of cultured keratinocytes with the characteristics of biological membranes. In cases where it's possible to prevent the deepening of deep dermal burns by applying RK within 10 days of injury, it is not necessary to transplant, healing is substantially accelerated and harvesting areas will be spared and repeated surgeries will be prevented. The RK with transplanted allogenic keratinocytes will temporarily adhere through healing; the keratinocytes will incorporate themselves into the regenerating epidermis, will proliferate, migrate, close the wound and will stimulate healing by producing various growth factors. The xenodermis will protect the wound and provides a natural substrate for migration of autologous keratinocytes. Within one week the allogenic keratinocytes are replaced by patient's own keratinocytes.

Example 5

Turkey Tendon

A tendon, harvested from the leg of a turkey, was rendered free of cells using the method in Example 1, and then it was affixed in an apparatus placed in a container, in which it was stretched over a roller and pulled by a line, to which a 12 kg weight was attached. It was immersed in 1% solution of aluminium chloride in this state, and left at 37° C. for 16 hours. Then the solution was exchanged 3 times using apyrogenic water, then with a mixture of 20 parts (by weight) of acetone and 10 parts (by weight) glycerine and 0.05 parts (by weight) of sodium chloride, and the structure was left in this solution for 25 hours under the tension created by the 12 kg weight and the stretching apparatus. Then the structure was dried, and together with the stretching apparatus it was moved into a vacuum drying chamber, preheated to 70° C., where it was rid of the remaining solvent in a two hour period, and furthermore a partial heat-induced denaturation of collagen occurred. The denaturation process was completed by heating to 88° C. for a period of 10 minutes, still under mechanical tension under nitrogen. The dried acellular implant, with a remaining water content of 3% (by weight) was enclosed in plastic sterilization packaging and was sterilized using 15 kGy of beta radiation using an electron accelerator. Sterility was ensured using a standard sterility test.

The acellular implant remained strong during rehydration and its diameter increased, whereas its length has contracted. After implantation, it was hydrated further due to a lowering cross-linking density, which can be defined, for instance, as a molar fraction of groups connecting two chains in a polymer. This also resulted in a gradual length contraction and the increase in pull on surrounding tissues, which can be advantageously used, for example, in reconstructive or orthopedic surgery.

Example 6

Porcine Small Intestine

A small intestine was harvested from a freshly slaughtered young pig, it was washed with water, turned inside out, and repeatedly soaked in an excess of 3% solution of sodium dodecyl sulfonate at 45° C. After this step, one end of the intestine was closed with a clamp, and on the other end it was connected to a source of demineralized water pressurized to 30 mm Hg (4 kPa). The overpressure was maintained in a bath of demineralized water at 40° C. for 24 hours. Then the demineralized water was exchanged for a solution of isopropyl alcohol and tert-butyl alcohol (1:1, by weight) and maintained at 70° C. under an inner overpressure of the alcoholic solution for another 6 hours. Finally, the mixture of alcohols was exchanged for methanol three times at room temperature. The acellular and dehydrated oriented membrane was then inflated with nitrogen and the outside was dried using a stream of clean air under a laminar hood, after which it was folded flat between two polypropylene plates and enclosed in a waterproof sterilization sack. It was then sterilized in two stages: in the first stage it was sterilized using 5 kGy of gamma radiation, then with a 15 kGy dose of accelerated electrons. The sterile acellular membrane is intended to be filled with a suspension of allogenic fibroblasts and implanted into the patient subcutaneously with the goal of regeneration of patient's subcutaneous connective tissue.

The invention claimed is:

1. A sterile, hydrophilic, substantially dehydrated, and partially denatured acellular matrix comprising collagen protein fibrils, wherein
   (i) the collagen protein fibrils are organized in a structural array oriented in the direction of a first spatial dimension having a first linear expansion coefficient, the first spatial dimension being perpendicular to a second spatial dimension having a second linear expansion coefficient,
   (ii) the first linear expansion coefficient is lower than the second linear expansion coefficient,
   (iii) the collagen protein content is from about 70% to about 95% by weight, and
   (iv) the acellular matrix has a porosity lower than about 70% by volume
   wherein the acellular matrix is prepared by the following steps:
   a) harvesting an animal tissue;
   b) forming an acellular matrix by removing cells from the tissue through the action of enzymes, surfactants, acids, alkalis, hypotonic aqueous solutions or their combination;
   c) dehydrating the acellular matrix by removing a significant amount of water, during which the matrix is maintained under mechanical tension in one or more selected directions;
   d) partially denaturating collagen structures in the acellular matrix through the action of increased temperature, organic compounds, polyvalent cations or their combination, while the matrix is maintained under mechanical tension in one or more selected directions; and
   e) sterilizing the dehydrated and partially denatured matrix using ionizing radiation.

2. The acellular matrix of claim 1, further comprising at least one of lipids and lipoproteins up to about 20% by weight.

3. The acellular matrix of claim 1, further comprising at least one of polysaccharides, glycoproteins, and glycoproteoglycans.

4. The acellular matrix of claim 1, further comprising at least one polysaccharide.

5. The acellular matrix of claim 1, further comprising at least one of softening, preserving, or bactericidal additives.

6. The acellular matrix of claim 1, wherein the collagen proteins are selected from the group consisting of collagen, elastin, fibrin, and keratin.

7. The acellular matrix of claim 1, wherein the animal source is a mammal.

8. The acellular matrix of claim 1, wherein the animal source comprises animal tissue, and wherein the animal tissue is skin, placenta, pericardium, dura mater, intestine, tendon or cartilage.

9. The acellular matrix of claim 1, wherein the acellular matrix is biodegradable.

10. The acellular matrix of claim 1, wherein the collagen protein fibrils are crosslinked.

11. The acellular matrix of claim 5, wherein the bactericidal additives comprise silver-protein complexes.

12. The acellular matrix of claim 5, wherein the softening additives and the preserving additives are water-miscible.

13. A method of manufacturing of the acellular matrix of claim 1, wherein the method comprises the following steps:
   a) harvesting an animal tissue;
   b) forming an acellular matrix by removing cells from the tissue through the action of enzymes, surfactants, acids, alkalis, hypotonic aqueous solutions or their combination;
   c) dehydrating the acellular matrix by removing a significant amount of water, during which the matrix is maintained under mechanical tension in one or more selected directions;
   d) partially denaturating collagen structures in the acellular matrix through the action of increased temperature, organic compounds, polyvalent cations or their combination, while the matrix is maintained under mechanical tension in one or more selected directions; and
   e) sterilizing the dehydrated and partially denatured matrix using ionizing radiation.

14. The method according to claim 13, characterized in that the partial denaturation of collagen structures is done with the aid of organic compounds miscible with water, selected from the group consisting of aliphatic alcohols $C_1$ to $C_4$, aliphatic aldehydes including formaldehyde and glutaraldehyde, aliphatic ketones including acetone and ethers including dimethyl ether, diethyl ether, dioxane and tetrahydrofurane.

15. The method according to claim 13, characterized in that partial denaturation of collagen structures is carried out at the temperature of 15° C. to 90° C.

16. The method according to claim 15, characterized in that partial denaturation of collagen structures is carried out at the temperature of 30° to 70° C.

* * * * *